US006458105B1

(12) United States Patent
Rippstein, Jr. et al.

(10) Patent No.: US 6,458,105 B1
(45) Date of Patent: Oct. 1, 2002

(54) DISPOSABLE SYRINGE HAVING A RETRACTABLE NEEDLE

(75) Inventors: Wayland J. Rippstein, Jr., Alvin, TX (US); Martin E. Smith, Camarillo, CA (US)

(73) Assignee: Maxxon, Inc., Tulsa, OK (US)

( * ) Notice: Subject to any disclaimer, the term of this patent is extended or adjusted under 35 U.S.C. 154(b) by 38 days.

(21) Appl. No.: 09/791,306

(22) Filed: Feb. 22, 2001

(51) Int. Cl.[7] .................................................. A61M 5/32
(52) U.S. Cl. ........................................ 604/195; 604/110
(58) Field of Search ................................ 604/195, 110, 604/187, 192, 218, 210, 263, 198

(56) References Cited

U.S. PATENT DOCUMENTS

| | | | |
|---|---|---|---|
| 4,425,120 A | 1/1984 | Sampson et al. | 604/198 |
| 4,643,200 A | 2/1987 | Jennings, Jr. | 604/198 |
| 4,675,005 A | 6/1987 | DeLuccia | 604/110 |
| 4,692,156 A | 9/1987 | Haller | 604/195 |
| 4,747,830 A | 5/1988 | Gloyer et al. | 604/110 |
| 4,790,822 A | 12/1988 | Haining | 604/110 |
| 4,816,022 A | 3/1989 | Poncy | 604/198 |
| 4,908,022 A | 3/1990 | Haber | 604/195 |
| 5,000,736 A | 3/1991 | Kaufhold, Jr. et al. | 604/110 |
| 5,125,898 A * | 6/1992 | Kaufhold et al. | 604/110 |
| 5,885,257 A | 3/1999 | Badger | 604/195 |
| 6,077,245 A * | 6/2000 | Heinrich et al. | 604/110 |
| 6,193,695 B1 * | 2/2001 | Rippstein, Jr. | 604/110 |

* cited by examiner

Primary Examiner—Patrick Brinson
(74) Attorney, Agent, or Firm—Browning Bushman, P.C.

(57) ABSTRACT

A disposable syringe assembly 10 including a cylinder body 12, a needle assembly 14, a piston assembly 16, a rear seal assembly 18, a hollow shaft 20, and a valve assembly having a valve port 61 and valve seals 49. The needle assembly may be releasably engaged with the cylinder body. The body and the piston assembly moveable within the body may define each of a fluid chamber 74 and an annular chamber 28. As fluid is drawn into the fluid chamber by movement of the piston assembly, air may be displaced from the annular chamber through the valve assembly. As fluid is discharged from the fluid chamber, the valve assembly may be closed and a vacuum created in the annular chamber. A valve positioner may control connector connectivity and valve port position. Near the end of the fluid discharge piston stroke, a connector 88 engaged with either the shaft of with the piston assembly may engage selectively engage a mating connector on the needle assembly. The needle assembly may be disengaged from the body. Thereafter, the axial fluid discharging, connecting and disengaging force may be removed and the needle assembly may automatically be retracted into the body to safely conceal the needle therein.

26 Claims, 7 Drawing Sheets

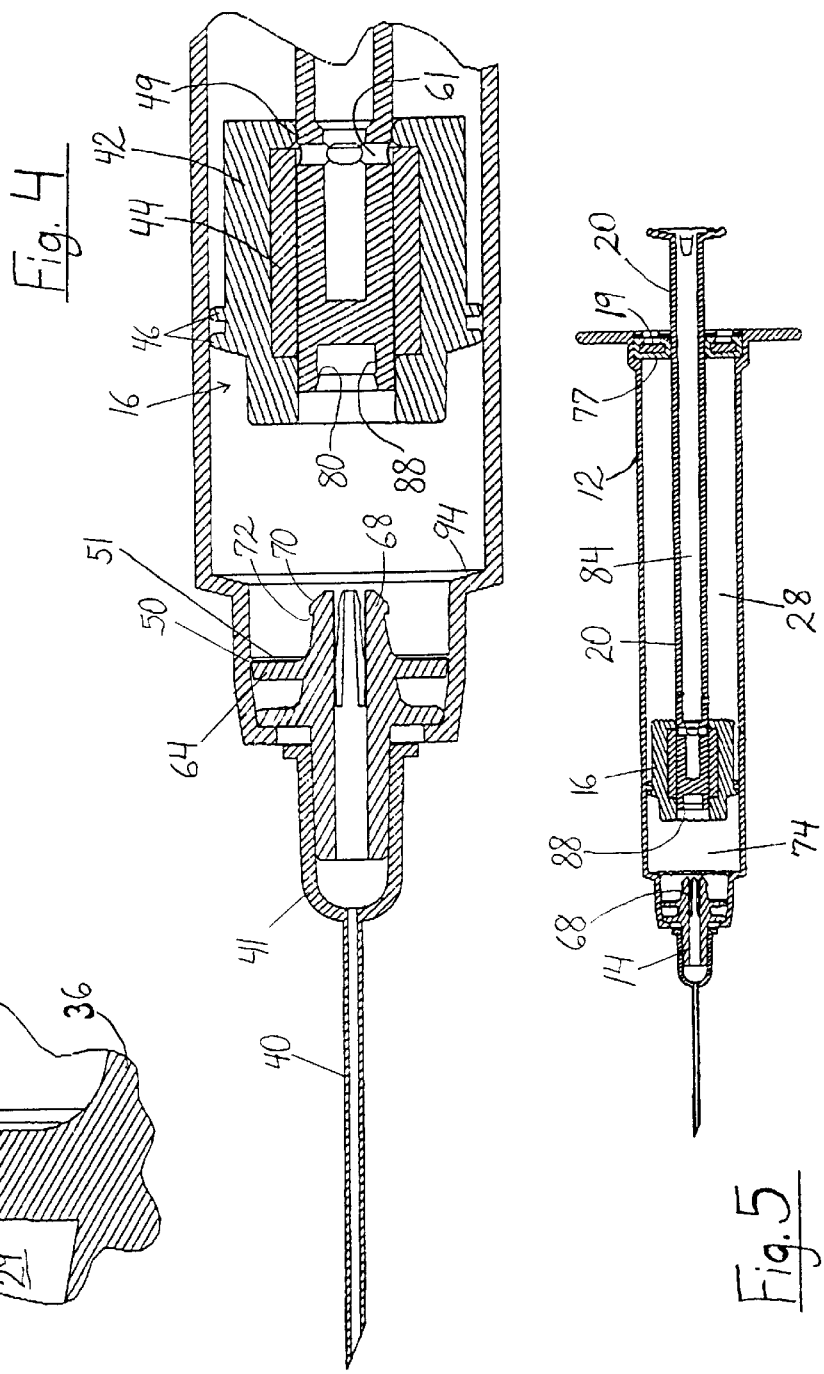

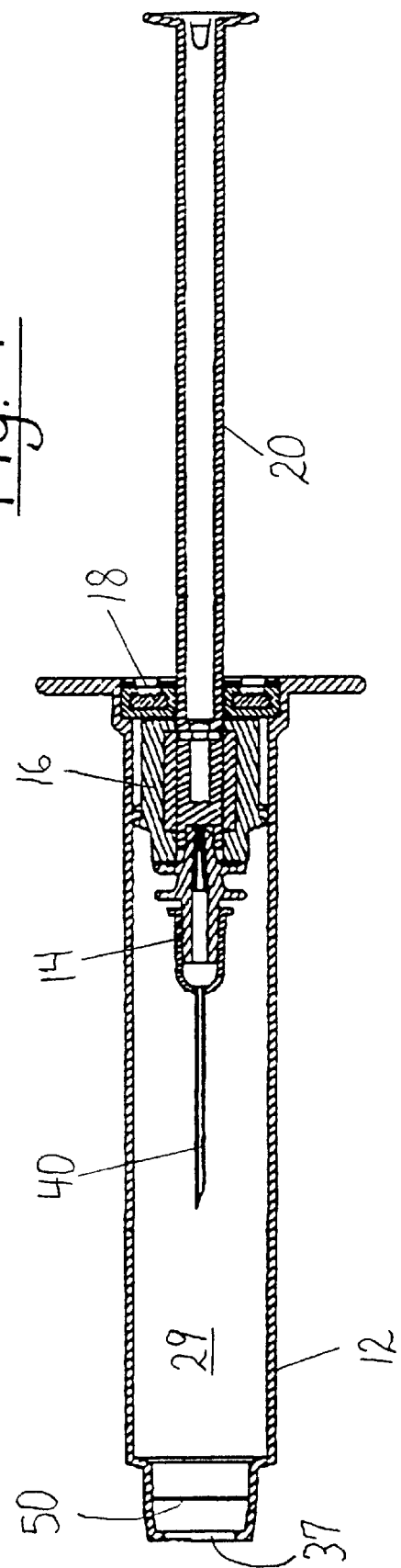

DISPOSABLE SYRINGE HAVING A RETRACTABLE NEEDLE

FIELD OF THE INVENTION

The present invention relates generally to medical instruments and more particularly to a disposable syringe having a retractable needle. More specifically this invention relates to a syringe which, during fluid injection or displacement of the contents from the syringe, a vacuum is created within the syringe body to automatically retract the needle into the inside of the syringe body after syringe use, to prevent accidental needlesticks.

BACKGROUND OF THE INVENTION

Health care workers routinely risk exposure to communicable diseases through accidental exposure to contaminated medical products, waste products and bodily fluids. One of the largest exposure risks to healthcare workers and handlers of related hazardous waste is from accidental needlesticks or scratches while using hypodermic syringes. The Centers for Disease Control and Prevention reports that there are in excess of one-half million reported accidental needlesticks each year and an estimated three million additional needlesticks not reported. It is further reported that the odds of a healthcare worker contracting human immunodeficiency virus (HIV) alone through a needlestick are one in 300. The odds of a healthcare worker contracting any of many other serious or potentially fatal diseases such as hepatitis are even greater. In response to this health issue some states and the federal government are enacting legislation requiring exclusive use of safety hypodermic syringes with retractable or protected needles, e.g., the federal Needlestick Safety and Prevention Act.

Numerous solutions to the needlestick problem have been proposed, including U.S. Pat. No. 4,790,822, which discloses a disposable syringe in which the needle can be captured by a plunger and then fully retracted into the barrel of the syringe. The plunger shaft may then be broken off flush with the end of the barrel such that the needle may not be mechanically projected to extend beyond the opposite end of the barrel.

U.S. Pat. No. 4,747,830 discloses a similar system including a plunger that can be broken off once the needle is fully retracted into the barrel of the plunger. U.S. Pat. Nos. 4,692,156 and 4,675,005 both disclose disposable syringes wherein the needle can be fully retracted into the barrel of the plunger. U.S. Pat. No. 4,643,200 discloses a similar system used with a blood donor assembly, which allows retraction of a needle into a barrel.

U.S. Pat. No. 4,425,120 discloses a movable needle guard conduit which extends from the barrel of the syringe over the full length of the needle. The needle guard may be retracted during use of the syringe and may then re-extend to cover the needle following use of the syringe. U.S. Pat. No. 4,816,022 discloses a syringe with a sliding cap which utilizes a nub and backseat for engagement of a nosepiece for securing the cap around the syringe. U.S. Pat. No. 3,008,570 discloses a removable cap for enclosing and protecting a sterilized syringe in a moveable housing.

U.S. Pat. No. 5,000,736 discloses a syringe including a tubular plunger from which air has been evacuated which upon use may retract the needle into the plunger by differential pressure. U.S. Pat. No. 5,885,257 discloses a syringe which utilizes a compressed spring placed between a needle carrier and the barrel of the syringe and including a releasable retaining means to hold the needle carrier in position until retraction is desired. U.S. Pat. No. 4,908,022 discloses a disposable safety syringe including a cylinder which is pre-filled with fluid medication, a double ended needle and a plunger. Following use of the syringe, the end of the needle which extends into the barrel may penetrate the piston such that the needle may be manually withdrawn into the barrel by axial retraction of the plunger which remains in engagement with the needle.

Thus, a variety of prior art retractable syringes are known. Prior art syringes, however, have not offered a universally acceptable solution to the needlestick issue. Healthcare workers throughout the world may benefit from a syringe which reduces or eliminates the risk of accidental needlestick or exposure to contaminated surfaces such as the exterior surface of a used needle, by overcoming the disadvantages of prior art syringes. An improved syringe is desired which is simple in design, manufacturing and operation so as to be widely applicable, cost effective, reliable and which does not require pre-filling with medication or fabricating with stored potential energy. A syringe is also desired which may become an industry standard through overcoming the disadvantages of prior art.

The disadvantages of the prior art are overcome by the present invention and an improved retractable needle syringe is hereinafter disclosed which has particular utility in protecting healthcare and sanitation workers.

SUMMARY OF THE INVENTION

The present invention is a hypodermic syringe apparatus (syringe) that may retract a hypodermic needle into a syringe body after the syringe contents have been discharged, so as to prevent accidental needlesticks, scratches or other exposure to healthcare workers of contaminated needles or fluids thereon. In addition to protecting healthcare workers, this invention may also prevent the multiple use or sharing of syringes and needles. This invention may also protect workers involved with disposal and sanitation of used syringes and may reduce the likelihood of infectious particulates becoming airborne. The syringe may preferably be a disposable, single use type and may be available in various standard and non-standard sizes and shapes.

It is an object of the present invention to provide an improved vacuum operated, retractable-needle syringe. A preferred embodiment of this invention may include: (a) a selectively retractable needle assembly including a hypodermic needle and needle seat apparatus for supporting and engaging the hypodermic needle; (b) a cylindrical syringe body to provide each of a reservoir for injectable or withdrawn fluids and a vacuum chamber; (c) a piston assembly to create pressure differentials within the cylinder body to draw fluids into the syringe body or discharge fluids contained within the syringe body, and to assist in producing a vacuum; (d) a hollow shaft and press plate for manipulation of the piston assembly; (e) a top seal for engaging and sealing with both the cylinder body and shaft to provide a pneumatic annular chamber within the cylinder body to retract the needle assembly, and (f) a valve assembly ton regulate air movement into and from within the annular chamber. All seals referenced herein are pneumatic and/or hydraulic seals.

The needle assembly may be selectively retractable in that a connector on the needle assembly may be selectively connected with a connector on the piston assembly and the needle assembly selectively and automatically retracted into the cylinder body. While moving the piston assembly relative to the cylinder body, the practitioner may discharge fluid into the fluid receptacle. In addition, the discharging piston stroke may close a valve assembly and create a substantial vacuum or low-pressure region within the annular chamber, which may be used thereafter to automatically withdraw the needle into the cylinder body once the injection is complete.

It is an object of the present invention to provide a piston and valve operated mechanism for creating and maintaining potential energy within the syringe, during use of the syringe for retracting the needle assembly upon completion of syringe use.

It is also an object of this invention to selectively connect a piston assembly with a selectively disengageable needle assembly. When the fluid is substantially fully discharged, a connector secured to the piston assembly may engage a connector secured to the needle assembly. A slight increase in axial force upon the shaft may attach the shaft and/or the piston assembly to the needle assembly. After needle assembly retraction the hypodermic needle may be fully encased and protected within the syringe body.

It is a feature of the present invention that the retractable syringe is simple to operate and economical to manufacture.

It is another feature of this invention that the syringe may be operated substantially by one hand, as required by many regulatory and safety codes and statutes.

It is also a feature of the present invention that the syringe is highly reliable and may fully perform its intended purpose, to facilitate a hypodermic injection and then fully retract and retain the used hypodermic needle within the syringe cylinder body immediately upon completion of use.

A significant feature of the invention is that the practitioner may utilize a syringe according to this invention in substantially the same order of operations as a conventional disposable syringe which does not automatically retract the needle.

Although preferred embodiments are disclosed, other embodiments may naturally evolve from the concepts of this invention and as such remain within the scope of this invention. Several alternative embodiments are disclosed in the attached drawings and detailed specifications. The concepts of this invention may be applied to syringes for use in hypodermic injections and withdrawals, including blood donation apparatus and related medical and technical equipment employing a potentially penetrating or scratching hypodermic needle or puncturing device.

The disadvantages over prior art are overcome by the present invention, and an improved disposable safety syringe having a retractable needle and an improved method of operating a hypodermic syringe and capturing a hypodermic needle inside a syringe body is disclosed.

BRIEF DESCRIPTION OF THE DRAWINGS

FIG. 4 is a cross-section view of a needle end portion of another embodiment of a syringe, illustrating the piston assembly prior to engagement with the needle assembly.

FIG. 5 is a cross-sectional view of the syringe in FIG. 4, from the needle assembly to the push plate.

FIG. 6 is a cross-sectional blowup view of a retaining assembly, retaining a needle assembly within a cylinder body.

FIG. 7 is a full length view of a syringe after full retraction of the needle assembly into the cylinder body.

DETAILED DESCRIPTION OF PREFERRED EMBODIMENTS

Figure 1:
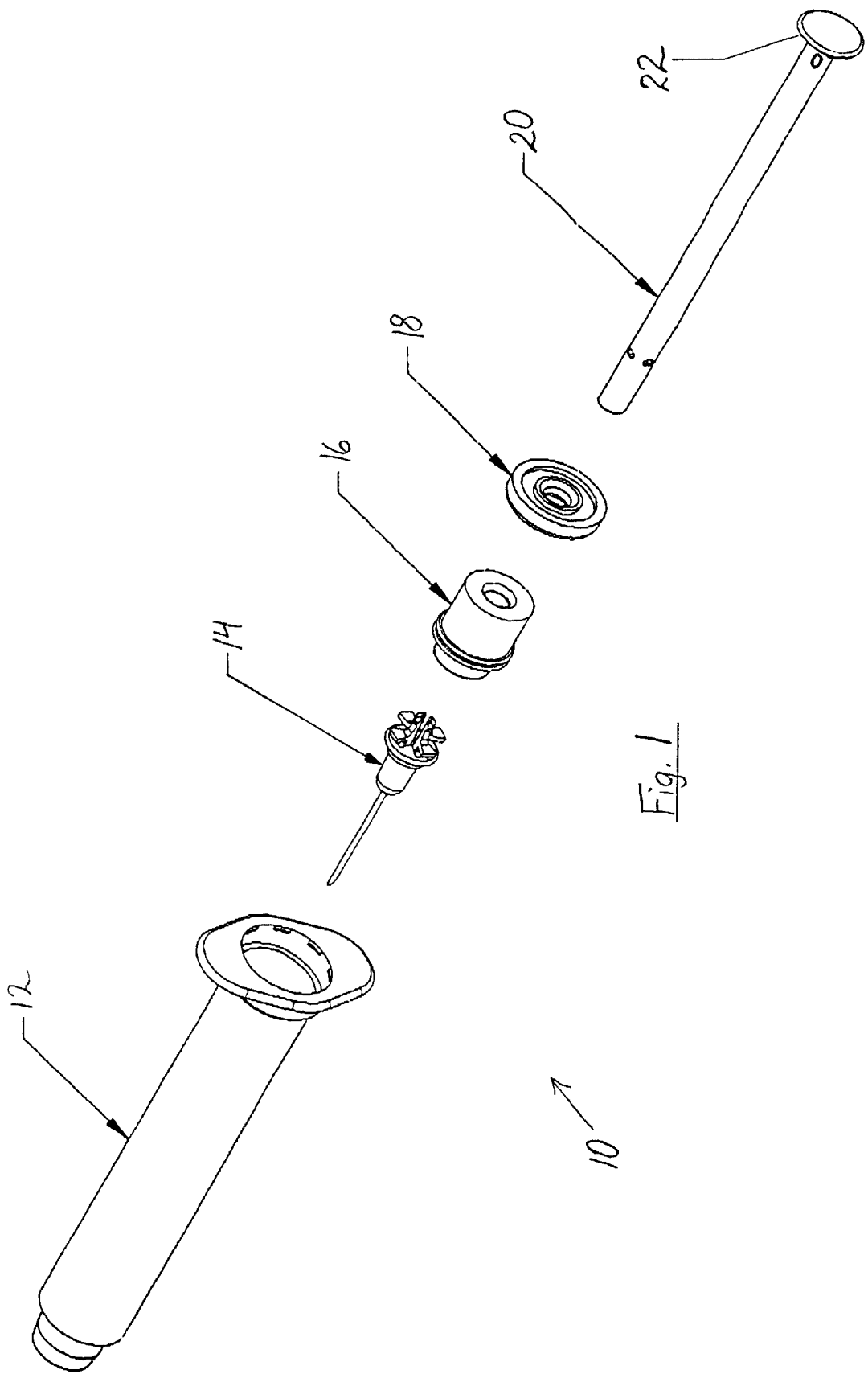
FIG. 1 is an exploded isometric view of a syringe illustrating the major component assemblies.

FIG. 1 illustrates a suitable embodiment for a hypodermic syringe apparatus that retracts a hypodermic needle into a syringe body according to the present invention. Referring to FIG. 1, the syringe apparatus 10 may generally include (a) a cylinder body 12; (b) a needle assembly 14; (c) a piston assembly 16; (d) a rear seal assembly 18; and (e) a hollow shaft 20. A valve assembly may be included, comprising seals between the piston assembly and the hollow shaft, and one or more ports 61 within the hollow shaft.

Figure 2:
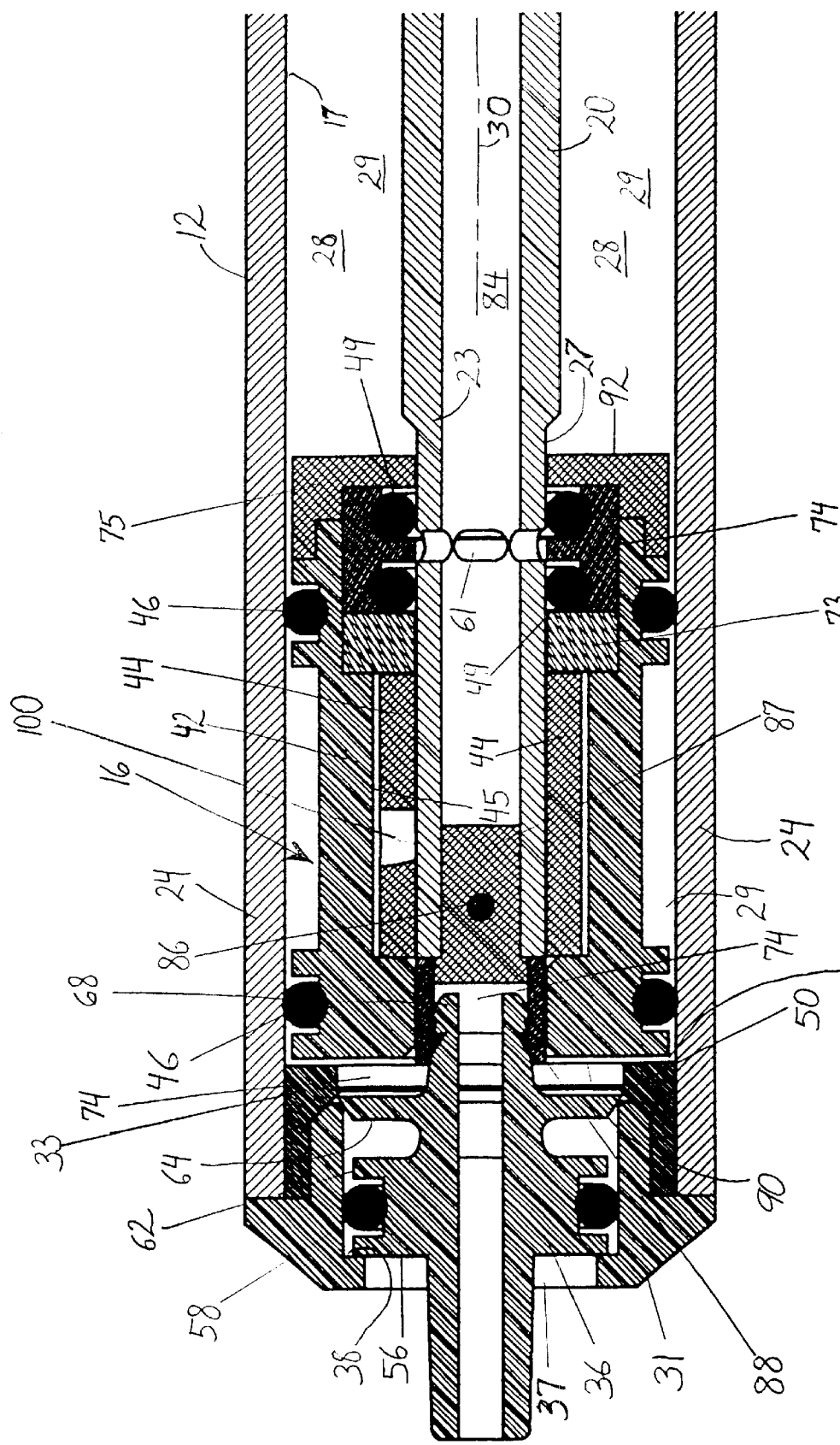
FIG. 2 is a cross-section view of a syringe assembly illustrating a detailed arrangement of various components near the needle end of the cylinder body.
Figure 3:
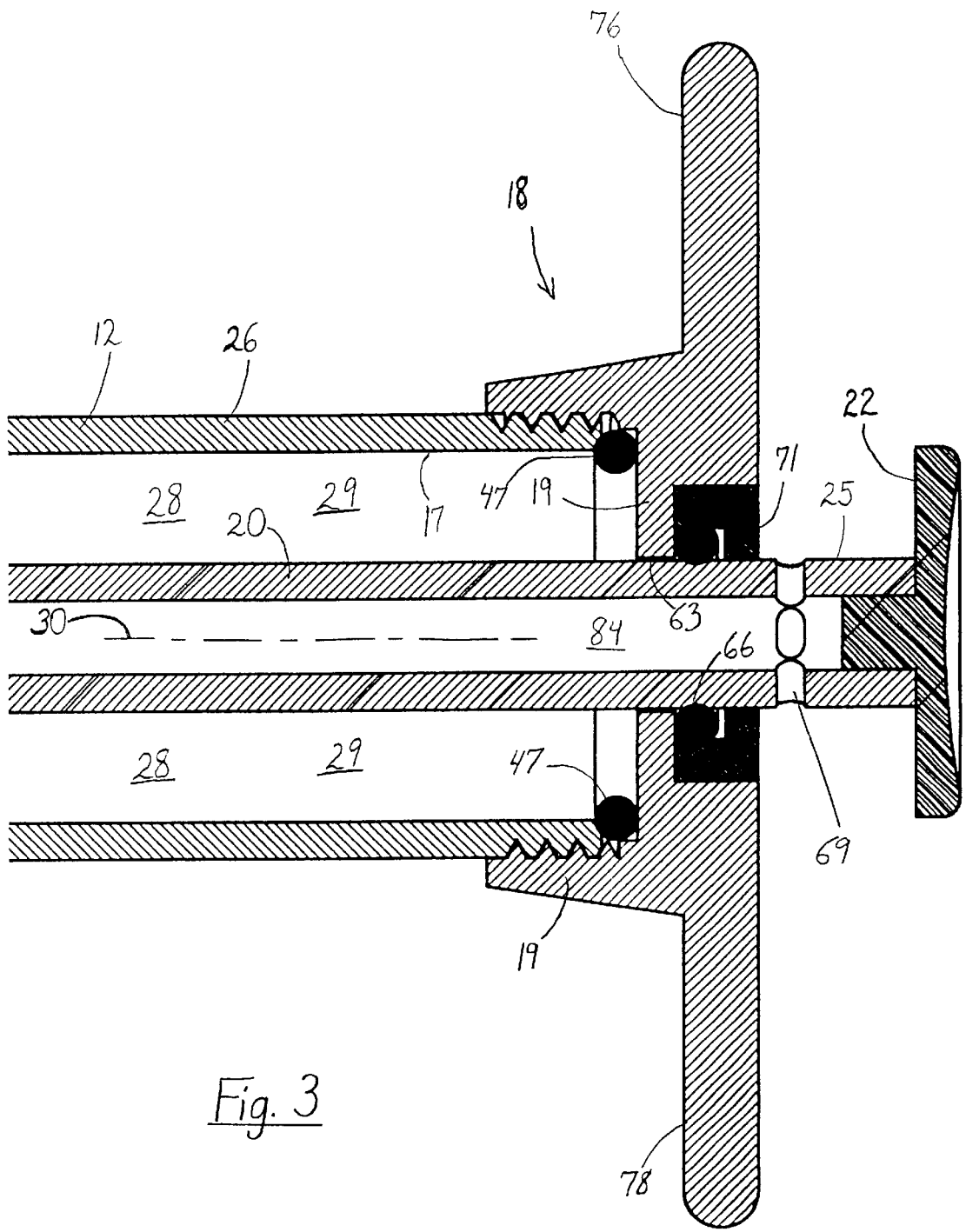
FIG. 3 is a cross-sectional view of the syringe in FIG. 2, illustrating a detailed arrangement of various components near the seal cap end of the cylinder body.

Those skilled in the relevant art will appreciate that each of the components of this invention may be configured in a number of varying arrangements, shapes and configurations. The component configurations illustrated in the Figures are illustrative of some preferred embodiments to illustrate operational principles and components functions and relationships. Variations may be made to accommodate manufacturing processes and operational requirements without departing from the spirit of the invention. As illustrated in FIGS. 2 and 3, the cylinder body 12 may include a needle end 24, an opposing end 26, and a throughbore 29 along a central axis 30 of the cylinder body. The central axis 30 may extend axially through the center of the throughbore 29, from the needle end 24 to the opposing end 26. Cylinder body 12 may include a portal opening 37 near the needle end 24 for sealingly receiving the needle assembly therein. The needle end of cylinder 12 may provide the portal opening in an end-piece 31 sealingly engaged with the cylinder 12. End-piece 31 may also be formed as an integral portion of the needle end of the cylinder body 12.

Referring to FIGS. 2 and 4, the needle assembly 14 may include a needle 40 engaged with a needle adapter 41. The needle adapter 41 may be sealingly engaged with a needle seat 36. Embodiments of the syringe assembly 10 may not include a needle 40 attached thereto. In fact, a substantial number of syringe assemblies are sold without a needle and/or a needle adapter. Either a needle, or a needle and adapter, may thus be marketed separately and added by the user. Because of such options, it may be understood to those skilled in the relevant art that the term needle seat, as used herein, may be defined broadly to include the component from which the needle or needle and needle adapter is supported. The term needle seat may thus refer merely to the structural component 36 sealingly engaged and supported within the needle end of the cylinder body, absent a needle 40 and/or a needle adapter 41. The term needle assembly, as used herein, includes a needle seat, and a needle and/or a needle and needle adapter attached thereto. Further, in other embodiments, the needle seat may be formed to include a needle 41 manufactured into the body of the needle seat.

In one preferred embodiment, a syringe assembly may include an annular stop lip 38 to engage a portion of the needle seat 36 to prevent discharge of the needle assembly/ needle seat from the needle end of the body 12. In lieu of stop lip 38, some embodiments may include a frustoconical portion of body 12 near the needle end 24 of the body 12 to support the needle assembly therein. The needle seat 36 may include a stop plate portion 56 for engagement with the annular stop lip 38. A "Lure-Lock" connector, as is well known in the industry, may be provided to secure the needle adapter 41 with the needle seat 36.

In the embodiment illustrated in FIG. 2, the needle seat 36 may support and retain the needle 40 in a static position relative to the needle seat 36, near the needle end 24 of the body 12. A needle assembly seal 58 may provide a fluid tight seal between the cylinder body 12 and the needle seat 36. All seals are presumed to be hydraulic and/or pneumatic seals. Seal 58 may be retained by radially extended portions 62 of the needle seat. Although an O-ring is illustrated, the seal between the needle assembly and the cylinder body 12 may be provided by an interference fit between components, by a seal gasket, by a viscous resin material, or other sealing mechanism. A preferred manufacturing material for substantially all components, except a needle 40, and possible a guide pin, may be manufactured from a plastic or resinous material. Other embodiments may also include some metallic components.

Referring to FIGS. 2 and 4, each illustrating slightly different embodiments of a syringe 10 according to the present invention, the needle seat 36 may be releasably retained within the cylinder 12 by a needle assembly retainer 50. The retainer 50 may releasably engage a portion of the needle assembly to retain the needle assembly in an initial retained position near the cylinder end of the body 12. The retainer 50 may permit the needle assembly 14 to be selectively disengaged from the retainer to release the needle assembly 14 from the initial retained position within the body 12 and moved to a needle disengaged position as illustrated in FIG. 7.

Referring To FIGS. 2, 4, and 6, the retainer 50 may be a raised lip extending circumferentially within the body 12. The retainer 50 may be formed as a homogenous portion of the cylinder body 12, as illustrated in FIGS. 4 and 6, or provided by a retainer member 33 immovably engaged with the body 12, as illustrated in FIG. 2. Retainer 50 may be shaped to conform to a corresponding mating groove 51 on a portion of the needle seat 36. One or more retaining plates 64 may be provided on the needle assembly, preferably with a knife-edge annular groove 51 for engagement with the retainer 50.

The portion of the needle seat 36 engaging the retainer 50 may be a relatively large OD portion 64 of the needle seat 36, such that the needle seat 36 may move past the retainer 50 without engaging it 50 when the needle assembly 14 is moved to the needle seat retracted position. In other embodiments, the retainer lip may be provided on the needle assembly and the retainer groove may be engaged with the cylinder 12.

The needle seat 36 may also include connector 68, illustrated as a plurality of male latching portions 68 in FIGS. 2, 4, and 5, each including a frustoconical outer surface 70 and a stop shoulder 72 for engagement with a mating connector stop surface 80, in connector mating connector 88. Mating connector 88 may be secured to the shaft 20 and be moveable relative to the piston assembly 16, moving with the shaft 20. Connectors 68 and 88 may be selectively and securely engaged with each other to connect the needle assembly 14 with the piston 16 assembly, and thereby permit the needle assembly 14 to be disengaged and safely retracted into the cylinder 12.

Figure 9:
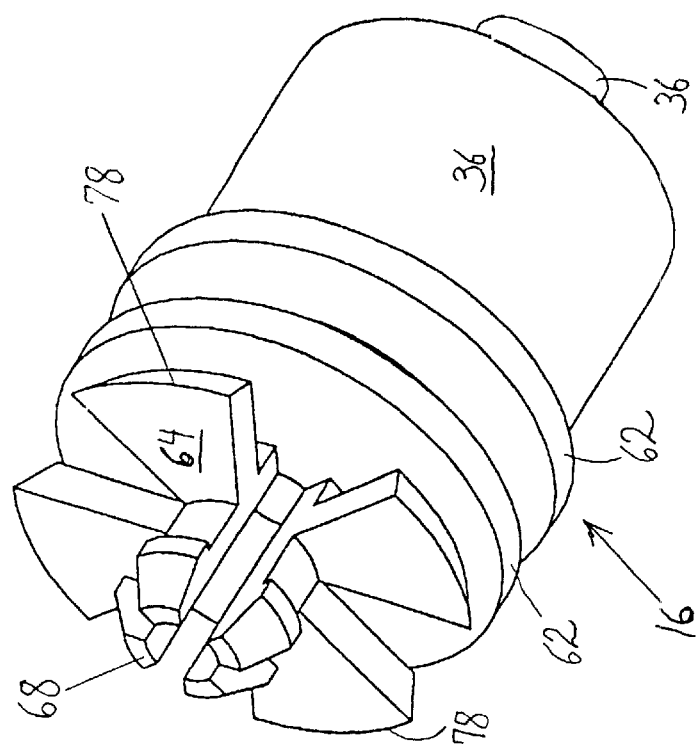
FIG. 9 is an isometric view of a needle assembly, illustrating an arrangement of connector and retainer components engaged with the needle assembly.

FIGS. 2, 4, and 9 illustrate an embodiment wherein the needle assembly 14 includes a plurality of four male connector portions 68 secured thereto. Four retainer plates 64 each including a knife edge 78 in lieu of groove 51 for engagement with a retainer 50 are also illustrated. In other embodiments, the needle seat 36 may include a female connector component for receipt therein of a male retainer component secured to either the shaft 20 or the piston body 42.

Referring to FIGS. 2 and 4, in a preferred embodiment the piston assembly 16 may be moveably positioned within the internal through bore 29 of the body 12, and may include a piston body 42. The piston assembly 16 may include a needle end 90 and an opposing shaft end 92. The shaft end 92 may face a rear seal cap 19 on the cylinder body 12, illustrated in FIG. 3. The piston assembly 16 may move axially along the centerline 30, and may include a shaft receptacle 45 within the piston body 42 and accessible by the shaft 20 from the shaft end 92 of the piston assembly 16.

The piston assembly 16 may include one or more outer seals 46 for sealing between the piston assembly 16 and an inner surface 17 of the piston body 12. FIG. 2 illustrates an embodiment providing a pair of O-ring seals 46, and FIG. 4 illustrates an embodiment wherein the seals are provided as an integral part of the piston 42, which may be formed form a pliable, resilient material capable of sealing with inner surface 17 during piston assembly movement.

A piston end of the shaft 20 may be moveably received within the shaft receptacle 45. The piston assembly 16 may include one or more inner piston seals 49 for sealing between the piston 42 and an outer surface 17 of the shaft 20, as illustrated in FIG. 2. In other embodiments, inner seals 49 may be formed as an integral port of shaft portion 27, or secured thereon.

Figure 8:
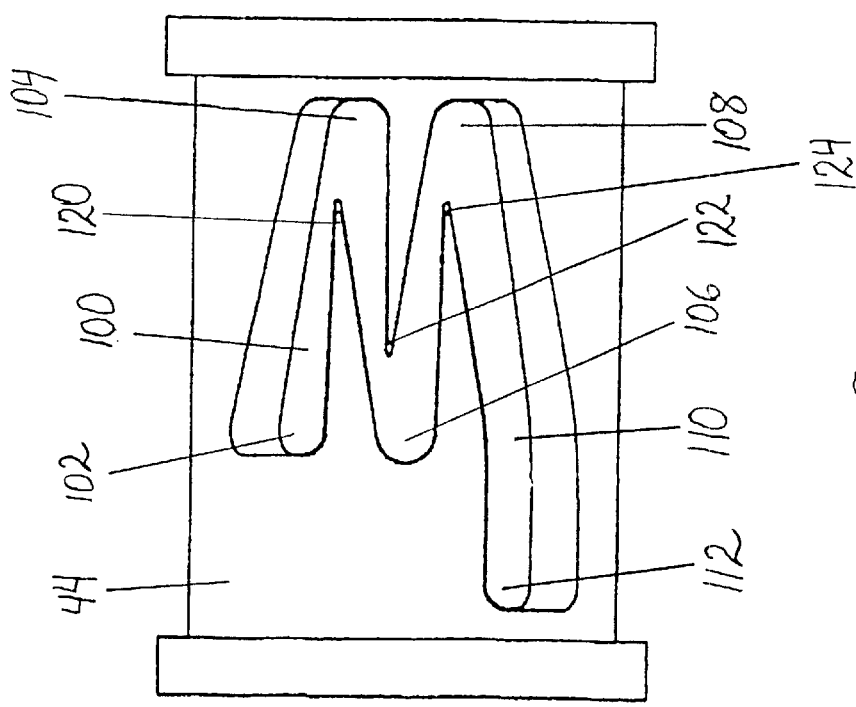
FIG. 8 is a side view of a spool-shaped valve port positioner including a W-shaped pin guide slot therein.
Figure 11:
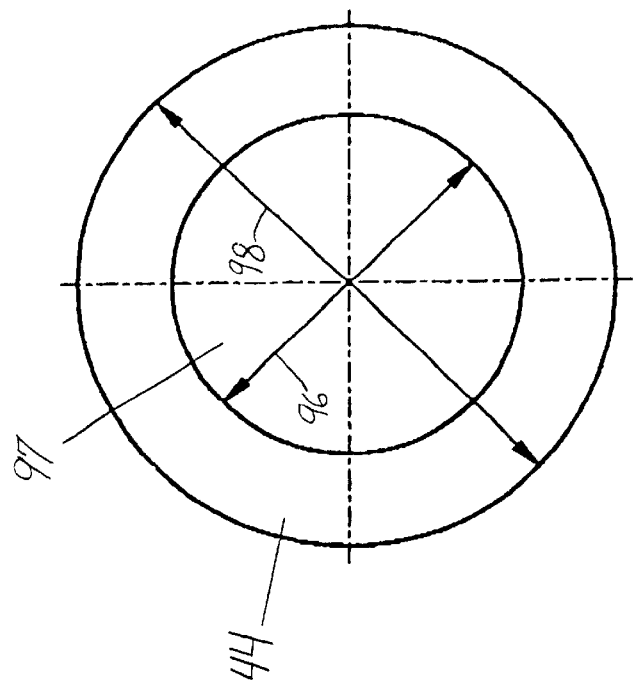
FIG. 11 is an end view of a valve port positioner, illustrating the through passageway having an ID and the positioner having an OD.
Figure 10:
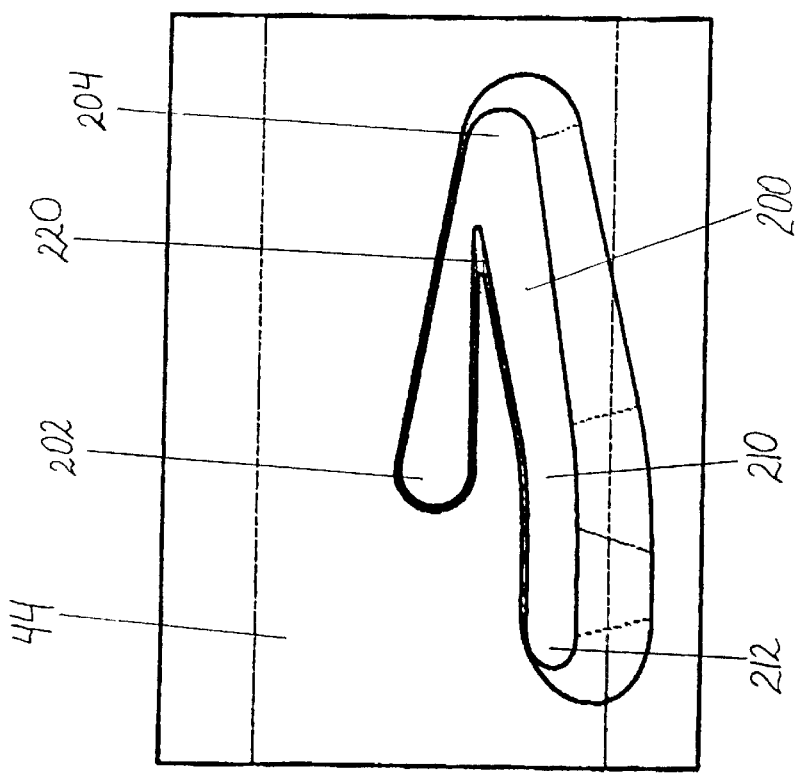
FIG. 10 is a side view of a sleeve-shaped valve port positioner including a V-shaped pin guide slot therein.

Referring to FIGS. 2 and 4, a preferred embodiment of the piston assembly 16 may include a valve port positioner 44 for regulating axial movement of the hollow shaft 20 relative to one or more valve assembly seals 49. The positioner 44 may be substantially sleeve-shaped or spool-shaped, as illustrated in FIGS. 10 and 8, respectively, and having a through bore for receiving a portion of the shaft 20 therein. The shaft 20 may move axially and/or rotationally relative to the port positioner 44. FIG. 11 illustrates an end view of a valve port positioner 44, including a through bore 97 having an internal diameter 96 for receiving the shaft 20 therein, and having an outer diameter 98 for positioning the positioner 44 within the shaft receptacle 45.

As illustrated in FIG. 2, the positioner 44 may be moveably secured within the shaft receptacle 45, such as by piston seal bushing 73, piston inner seal support member 74, piston inner seal retainer cap 75, and by one or more inner seal members 49. FIG. 4 illustrates a simplified embodiment wherein the inner piston seal may be provided by interference fit of the shaft 20 with a portion of the piston body 42. In such embodiment, the piston body 42 may be formed from a pliable, resilient material that may sealingly engage the shaft 20 while the shaft 20 moves relative to the piston body 42.

As shown in FIGS. 2, 3, 4, 5 and 7, the shaft 20 may be a hollow shaft 20 having a piston end 23 and a push plate end 25. A substantially disk shaped push plate 22 may be affixed to the push plate end 25 of the shaft 20 for applying axial force to the shaft with an operator thumb or finger. The push plate 22 may also include any type of device or component to facilitate manual or automatic manipulation of the shaft 20 with respect to the body 12 and thereby manipulate the piston assembly 16. In one embodiment, such as illustrated in FIG. 3, each of the index and middle fingers may be positioned under a respective flange finger plate 76 and 78. Thereby, the thumb may then be placed on the push plate 22 to apply substantial downward force to the shaft 20.

An elongate passageway 84 may be provided within the shaft 20 and may extend from substantially the piston end 23 to the push plate end 25. The passageway 84 may be in atmospheric fluid communication with the atmosphere external to the body 12 and the shaft 20, through atmosphere ports 69, positioned in the push plate end 25 of the shaft 20, as illustrated in FIG. 3. The piston end 23 of the shaft 20 may include a shaft closure 87, such as a plug, to seal the piston end of the passageway 84.

The hollow shaft may also include a valve port 61 to permit air within annular chamber 28 to be conducted between the chamber 28 and the shaft passageway 84. The valve port 61 may be selectively axially positioned to create a valve assembly that is moveable between a valve opened position and a valve closed position. The valve ports 61 may be axially positioned in the shaft such that as the shaft 20 moves relative to the piston assembly 16, the valve ports move past at least one inner seal 49.

The valve port 61, the inner seals, an outer surface 27 of the shaft 20, the valve port positioner 44 and the movement of the shaft and valve port 61 relative to the seals 49 may comprise a valve assembly. The valve assembly may be operable between a valve opened position and a valve closed position. In the valve opened position, the ports 61 may be on an annular chamber side of the seal 49, and air may be conducted into and from within the pneumatic annular chamber 28, through the hollow shaft passageway 84 and through atmosphere ports 69. In the valve closed position, the ports 61 may be axially positioned on a needle assembly side of seal 49, and no air may be conducted into or out of the annular pneumatic chamber, as ports 61 will not be in fluid communication with the annular chamber 28.

A positioner pin 86 may be provided on or secured to the hollow shaft 20. The positioner pin 86 may extend radially above the outer surface 27 of the hollow shaft 20, and extend radially into at least a portion of the valve port positioner 44. The valve port positioner may include a slot for receiving the extended portion of the positioner pin 86 moveably within a pin guide slot 100. The positioner pin 86 may selectively move axially within the pin guide slot 100. Each of the positioner pin 86 and the port positioner 44 may move rotationally with respect to the other, thereby allowing the pin to move through an angular slot configuration, such as illustrated in FIGS. 8 and 10. The positioner 44 may control the opening and closing of the valve assembly by controlling the position of the valve port 61 relative to the valve seal 49. The positioner may also control the position of the connector 88 with respect to connector 68.

A rear seal cap assembly 18 may be provided in pneumatic sealing engagement with the opposing end 26 of the cylinder body 12. A seal cap member 19 may be engaged with an opposing end of the cylinder body and sealed thereto, such as by seal 47. A shaft passageway 63 may permit the shaft 20 to be positioned through the seal cap 19. The push plate end 25 of the hollow shaft 20 may be axially positioned through a passageway 63 in the seal cap assembly 18. Seal cap shaft seal 66 may provide a seal between the outer surface of hollow shaft 20 and the seal cap 19 as the shaft 20 reciprocates through passageway 63. Seal 66 may be retained within the seal cap 19 by seal retainer 71. FIG. 5 illustrates an embodiment wherein seal cap assembly seals 47 and 66 are replaced by a common seal cap seal member 77, simultaneously sealing between seal cap 19 and cylinder 12, and between seal cap 19 and shaft 20.

The piston assembly 16 sealingly positioned within the throughbore 29 may substantially divide the cylinder throughbore 29 in two chambers. A fluid chamber 74 may be created within the cylinder 12 substantially between the needle assembly 14 and the needle end 90 of the piston assembly 16. A pneumatic annular chamber 28 may be created in the annular volume within the cylinder 12, between the shaft end 92 of the piston assembly, the seal cap assembly 18, and an exterior surface of the shaft 20. As the piston assembly 16 moves axially within the cylinder 12, the volume of fluid chamber 74 changes inversely proportional to the change in volume of the pneumatic annular chamber 28.

Referring to FIGS. 2 and 8, one embodiment of a valve port positioner 44 may include a substantially "W-shaped" pin guide slot 100. A syringe 10 may be provided to a practitioner/syringe operator with the piston assembly 16 positioned within the through bore 29, substantially near the needle end 24 of the cylinder body 12. In such embodiment, the positioner pin 86 may be located at position 102. The needle end 92 of the piston assembly may be engaged with a stop surface affixed to the cylinder 12, such as stop surface 94. With the positioner pin 86 in position 102, the shaft 20 will be axially positioned with the valve port 61 in a valve opened position, and connector 88 axially separated from connector 68. Axial force upon the shaft to attempt to move connector 88 into engagement with connector 68 will be prohibited by pin 86 engaging the end of the slot at position 102.

During manual syringe operation, a practitioner may apply opposing axial forces upon the cylinder 12 and shaft 20 to cause the shaft 20 to move toward the opposing or seal cap end of the cylinder 12. During initial movement of the shaft 20 relative to the cylinder 12, the piston assembly 16 may not move axially, while pin 86 moves from position 102 to position 104. When the pin 86 engages the positioner body at the end of the slot at position 104, the piston assembly 16 may move with the shaft 20 toward the opposing end 26 of the cylinder 12. During this movement, the valve port 61 remains in a valve opened position, such that air within the annular chamber 28 may be expelled to the atmosphere external to the syringe through ports 61 and 69, and through passageway 84. Air may simultaneously enter the liquid chamber 74 through the needle 40.

As the pin moves from position 102 to position 104, it may move through a narrowing of the slot caused by positioner 44 sleeve point 120 being formed at a slight angle with respect to an opposing side of the slot. As the positioner 44 may preferably be formed from a pliable material, the point 120 may elastically spread slightly as the pin moves past point 120 to point 104. Thereafter, point 120 may elastically flex back to its initial position and act as a check or switch to prevent the pin 86 from traversing to point 102 during subsequent pin movement.

The practitioner may then insert the needle 40 into a vial or other fluid source and press shaft 20 toward the needle end 24 of the body 12 to expel the air from fluid chamber 74 and pressurize the vial. During the initial movements of the shaft toward the needle end of the cylinder, the piston assembly 16 may not move. The shaft may move relative to the piston assembly and move pin 86 from position 104, past point 120 and along a path to position 106. In moving to position 106, the pin 86 may move past a second flexible switch point 122, thereby preventing return of the pin to position 104 during subsequent movements. As pin 86 engages the positioner 44 at point 106, the piston assembly may thereafter move along the cylinder 12 with the shaft 20. With the pin in position 106, movement of the shaft into the shaft receptacle is limited by the pin 86, such that the valve port 86 remains in a valve opened position, permitting air to enter the annular chamber 28. In addition, when the piston assembly stop surface 94, the connectors 88 and 68 may not engage with each other due to the relative axial position of the shaft relative to the positioner 44 due to the pin engagement in position 106.

With the needle 40 inserted into the vial, the practitioner may then begin withdrawing the shaft 20 from the body 12, thereby drawing fluid into the fluid chamber 74. Those skilled in the art will appreciate that the pressuring of the vial with the air as discussed above is not mandatory, but may be desirable in some instances so that fluid under pressure may be easily drawn into the syringe. During initial movement of the shaft relative to the piston assembly 16, the pin 86 may move from position 106, past a third check/switch point 124, and to position 108. When the pin 86 reaches point 108, the pin may engage the positioner 44 and permit the piston assembly to move toward the seal cap end of the syringe, thereby drawing in a determined amount of liquid. The syringe body 12 may include indexing or marking on an outer surface of the cylinder 12 to indicate fluid volumes within the fluid chamber 74 at various piston assembly positions relative to the cylinder.

Preferably, the syringe selected by the practitioner may be sized such that the desired amount of fluid to be drawn into the syringe is substantially near the maximum volume of the syringe, such that the liquid drawing shaft stroke may be a nearly full stroke. In the event the syringe is substantially larger than the needed amount of liquid, the practitioner may remove the syringe form the file, hold the needle upright and draw air into the remaining portion of the liquid chamber 74, such that a substantially full draw stroke is made. Thereby, the piston assembly may be relatively near the seal cap assembly. However, a fluid drawing stroke of approximately one-half of the volume of the syringe or greater may be sufficient to permit creation of sufficient vacuum within the cylinder to automatically retract the needle safely within the cylinder 12. The The practitioner may then remove the syringe from the vial, hold the syringe upright with the needle above the shaft, and expel any air from the liquid chamber and expel any excess liquid, until the correct amount of liquid remains in the syringe. During the initial fluid expelling or discharging movement of the shaft toward the needle assembly, the shaft 20 may move relative to the piston assembly, while the piston assembly may remain substantially stationary. Positioner pin 86 may move from position 108, past check/switch 124, toward point 112. In so moving, the valve port 612 may move from the valve opened position at position 108, toward a valve closed position. When the pin is at position 110, which is substantially axially the same position a positions 102 and 106, the valve port 61 may begin moving past inner seal 49 to a valve closed position. Thereby, no additional air may enter the pneumatic annular chamber 28 when the valve port is in the valve closed position.

The needle 40 may be inserted into the receptacle or fluid receiving body prior to expelling or discharging the desired amount of fluid from the fluid chamber 74. As movement of the shaft 20 relative to the piston assembly 16 moves pin 86 past positioner position 110, moving the valve assembly to the valve closed position, the pin 86 will engage the positioner 44 at position 112. The pin engagement may permit axial movement of the piston assembly with the shaft toward the needle assembly to expel or discharge the fluid from the fluid chamber 74 and into the receptacle or receiving body.

Movement of the pin 86 past position 110 to position 112 also permits the shaft 20 to move axially relative to the positioner 44 and the piston assembly 16 such that when the piston assembly 16 engages stop surface 94 or substantially immediately prior thereto, connector 68 may engage connector 88. A slight increase in axial discharge pressure upon the shaft by the practitioner may permit the two connectors 68 and 88 to securely connect or engage each other.

Referring to FIGS. 4, 5, 6, and 7, as the valve assembly is in the valve closed position while the piston assembly 16 is moved from the opposing or seal cap end of the syringe toward the needle assembly end of the body, substantially no air was permitted to enter the pneumatic annular chamber 28. Thereby, piston assembly movement created a vacuum or low pressure region in chamber 28, having an internal pressure less than the substantially atmospheric pressure on the needle end of the piston assembly. A W-shaped slot 100 in the positioner 44 permits a valve assembly that includes multiple valve opened positions 102, 104, 106, and 108, and one valve closed position 112.

As the practitioner relaxes or releases axial pressure upon the shaft 20, the pressure differential created across the piston assembly 16 may permit disengagement of the needle assembly 14 from the retainer 50. As illustrated in FIG. 7, thereafter, the needle assembly 14, being secured to the piston assembly 16, may move axially into the cylinder body 12 as the piston assembly is automatically retracted toward the seal cap end of the body 12 by the pressure differential across the piston assembly. The needle 40 is also thereby drawn into the body 12 and retained therein due to the needle assembly being secured to the piston assembly. To prevent the shaft from moving the piston assembly and engaged needle assembly toward the needle end of the cylinder, the shaft may be broken off near the seal cap, or a locking mechanism, such as s clip or friction lock may secure the shaft from moving relative to the cylinder 12. A practice of breaking the shaft may prevent accidental manual projection of the needle assembly 14 from the body 12. In addition, it may discourage subsequent use of a disposed syringe assembly for illegal drug use.

Upon attachment of the connectors and injection of the fluid, the axial connecting and disengaging force applied by the practitioner upon the shaft may be relaxed. The ambient atmospheric pressure external to the needle assembly and piston assembly may act axially through the needle assembly, through the needle end of the cylinder body, and upon the needle side of the piston assembly, in the axial direction of the rear seal. This pressure force may be referred to as a gross retracting force. The gross retracting force acts in opposition to an opposing force created by atmospheric pressure acting axially upon the piston stem, in the direction of the needle assembly. The opposing force is created by the reduced pressure in the annular chamber acting upon the annular area on the seal assembly side of the piston assembly. The ambient atmospheric pressure also acts upon a larger piston surface area than the opposing force. The net result is that the gross retracting force is substantially larger than the opposing force. The difference in the gross retracting force and the opposing force results in a net retracting force upon the piston assembly and engaged needle assembly in the axial direction of the seal cap assembly. The magnitude of the net retracting force may be sufficient to disengage and move the piston assembly and needle assembly to a retracted position within the cylinder body. In the event that after completion of automatic retraction a portion of the needle 40 remains exposed beyond the end of the cylinder assembly 12, the practitioner may manually complete the retraction of the needle assembly into the cylinder body 12 by exerting a small pull force on the shaft 20.

Other embodiments of the syringe may include a positioner having substantially a "Z" shaped slot or a "V" shaped slot, each providing a modification on the operation of the W shaped slot, but with functional properties consistent with the operations described in the "W" slot. Each slot configuration still involves moving a hollow, air conducting shaft relative to a piston to operate a valve assembly between one or more valve opened positions and at least one valve closed position.

FIG. 10 illustrates an embodiment of a positioner including a "V" shaped slot 200. The positioner pin 86 may be initially positioned in position 202, with the piston assembly near the needle assembly, and the valve assembly in the valve opened position. The needle 40 may be inserted into a vial.

Drawing back on the shaft may initially move the pin 86 from position 202 in the V shaped slot, past the check/switch 220, and to position 204 where the pin 86 engages the positioner at the end of the slot 200. Continued axial drawing force on the shaft may move the piston assembly toward the seal cap until a full draw stroke is made and the piston assembly engages the seal cap assembly. Liquid may be drawn into the syringe until the desired amount of liquid is contained within the liquid chamber 74, the needle removed from the vile, and if needed air may be drawn into the liquid chamber to complete the draw stroke to a full stroke, such that the piston assembly is substantially near the seal cap assembly.

Thereafter, an axial pushing or fluid discharging force may be applied to the shaft, initially moving pin 86 from position 204, past the check/switch 220, and toward position 212. When the pin moves past position 210, the valve port 61 may move past seal 49, closing the valve assembly, thereby prohibiting substantially any additional air from entering the annular chamber 28.

As the pin 86 engages the end of the V shaped slot 200 at position 212, the pin may engage the positioner 44. Further exertion of force upon the shaft may move the piston assembly toward the needle assembly. In moving past position 210 to position 212, the shaft 20 also may move axially sufficient relative to the piston assembly such that the connector 88 may be positioned to connect with connector 68 upon engagement therewith, near the bottom of the discharge stoke.

Air and excess liquid may be discharged from the fluid chamber 74 by piston assembly movement toward the needle end of the cylinder. Such movement may also create the pressure drop across the piston, since the valve assembly is in the valve closed position. If a partial movement of the piston assembly toward the needle assembly is made prior to insertion of the needle into the receiving body or receptacle, the axial position of the piston assembly may need to be temporarily secured while the needle is being inserted into the receiving body to prevent the pressure drop across the piston assembly from moving the piston assembly. Such securing of the piston assembly may be done by the practitioner holding axial force on the shaft, or by a selectively releasable clip or locking mechanism (not shown), such as a friction type lever-lock. The needle 40 thereafter may be inserted into the fluid repository or receiving body.

Continued application of axial force upon the shaft 20 may release a clip or locking mechanism, if any, discharge the fluid from the fluid chamber 74, and connect connectors 68 and 88. Releasing the axial force permits the differential pressure across the piston assembly to disengage the needle assembly from the cylinder 12, and automatically retract the needle 40 and needle assembly with the piston assembly into the cylinder, near the seal cap assembly.

Other embodiments of the syringe may include a retainer mechanism in which disengagement of the needle assembly is at least partially effected by the practitioner applying an axial retainer shearing force to the shaft, near the end of the fluid discharging piston stroke. Thereby, the needle assembly may be at least partially disengaged from the cylinder, such that the created vacuum may complete the disengagement, if necessary, and automatically retract the needle assembly into the cylinder body.

Alternative embodiments may provide the guide pin slots within a portion of the shaft, and the guide pin secured to the piston assembly or a positioner sleeve. The operation of the pin within the slot may be similar to the operations described above. Still other embodiments may place the female connector on the needle assembly and the male connector on the shaft for engagement with the female connector. Connectors also may be configured as grapple-type catches. Components may be threadably secured to each other, or bonded to each other. Components may be fabricated from a variety of materials, including thermo-plastic resins, softer pliable materials, metals or silicone base materials, such as glass and ceramics. A preferable material may be a combination of rigid plastics and pliable thermo plastic materials, as appropriate.

In other alternative embodiments, after retraction of the needle assembly into the body 12, the tip of the needle 40 may be reoriented off the central axis 30 to an angular position with respect to the central axis 30. Such re-orientation may be performed by a connector assembly that allows gravitational angular movement of the needle 40 with respect to the central axis. A biasing member may also be provided to re-orient the tip of the hypodermic needle toward an inner wall 17 of the cylinder body 12. Such reorientation may discourage or prevent re-use or the needle accidentally re-projecting from within the cylinder assembly 12. The pressure differential across the piston also may remain due to the pneumatic seals 18 and 46, such that the piston may not allow connected needle assembly 36 to move and expose needle 40 from within the body 12. The act of connecting the connectors or another final component movement may release a glue or other liquid within the syringe which may cause the needle assembly and/or the piston assembly to be secured to the cylinder 12.

It may be appreciated that various changes to the components, methods or steps herein, as well as in the details of the illustrated apparatus, methods and systems may be made within the scope of the attached claims without departing from the spirit of the invention. While preferred and alternative embodiments of the present invention have been described and illustrated in detail, it is apparent that still further modifications and adaptations of the preferred embodiments will occur to those skilled in the art. However, it is to be expressly understood that such modifications and adaptations are within the spirit and scope of the present invention, which is set forth in the following claims.

What is claimed is:

1. A syringe for retracting a needle attached to a needle seat, the needle being in sealed engagement with the needle seat, comprising:

a cylinder body having a needle end and an opposing end, the cylinder body having a central axis and an internal throughbore extending between the needle end and the opposing end, the cylinder body receiving the retracted needle seat therein;

a needle seat in sealed engagement with the cylinder body when the needle seat is in an initial retained position, and the needle seat being selectively moveable from the initial retained position to a needle seat retracted position;

a piston assembly moveably positioned within the internal through bore of the cylinder body, the piston assembly having a needle end and a shaft end, the piston assembly including a piston for axial movement within the internal throughbore, a shaft receptacle within the shaft end of the piston assembly, the piston assembly sealing between the piston and an inner wall of the cylinder body while axially moving within the internal throughbore;

a hollow shaft having a piston end and a push plate end, the piston end positioned within the shaft receptacle and axially moveable relative to the piston assembly, and the push plate end positioned external to the cylinder body, the hollow shaft moveable relative to the cylinder body for axially moving the piston assembly within the through bore of the cylinder body;

a connector for selectively attaching the needle seat to one of the hollow shaft and the piston assembly;

a rear seal cap in sealing engagement with the opposing end of the cylinder body and in sealing engagement with the moveable hollow shaft for effecting an annular chamber inside of the cylinder body, outside the shaft, and between the piston assembly and the rear seal cap; and a valve assembly operable in response to axial movement of the hollow shaft between at least one valve opened position for evacuating air from within the annular chamber and a valve closed position for prohibiting the entry of air into the annular chamber, such that movement of the hollow shaft moves the valve assembly to the valve closed position and subsequent axial movement of the piston assembly toward the needle end of the body creates a vacuum in the annular chamber to automatically move the needle seat to the needle seat retracted position.

2. The syringe assembly as defined in claim 1, further comprising:

the hollow shaft having a shaft passageway extending substantially from the piston end to the push plate end for conducting air between the annular chamber and the atmosphere external to the syringe assembly when the valve assembly is in one of the at least one valve opened positions;

a passageway closure to pneumatically close the piston end of the shaft passageway; and the valve assembly including one or more valve assembly seals for sealing between the piston and an outer surface of the hollow shaft.

3. The syringe assembly as defined in claim 2, wherein the valve assembly further comprises:

a valve port in the hollow shaft for conducting air between the annular chamber and the shaft passageway when the valve assembly is in one of the at least one valve opened positions; and a valve port positioner for regulating axial movement of the hollow shaft relative to the one or more valve assembly seals and thereby moving the valve port relative to the one or more valve assembly seals between the at least one valve opened position and the valve closed position.

4. The syringe assembly as defined in claim 3, wherein the valve port positioner further comprises:

a pin guide slot secured to one of the piston end of the hollow shaft and the piston assembly for regulating movement of a positioner pin within the pin guide slot; and the positioner pin secured to the other of the piston end of the hollow shaft and the piston assembly for moving within the pin guide slot during movement of the valve port between the at least one valve opened position and the valve closed position.

5. The syringe assembly as defined in claim 4, wherein the pin guide slot further comprises:

a W-shaped slot having five stop positions for positioning the positioner pin relative to the pin guide slot during successive axial movements of the hollow shaft relative to the piston assembly, and wherein a final axial movement moves the valve port from one of the at least one valve opened position to the valve closed position to prevent air from entering the annular chamber as the piston assembly is moved from the opposing end of the cylinder body toward the needle end of the cylinder body.

6. The syringe assembly as defined in claim 4, wherein the pin guide slot further comprises:

a V-shaped slot having three stop positions, each for positioning the positioner pin relative to the pin guide slot during successive axial movements of the hollow shaft relative to the piston assembly, and wherein a final axial movement moves the valve port from one of the at least one valve opened position to the valve closed position to prevent air from entering the annular chamber as the piston assembly is moved from the opposing end of the cylinder body toward the needle end of the cylinder body.

7. The syringe assembly as defined in claim 4, wherein the valve port positioner is formed from a pliable material and at least a portion of a pin guide slot has a variable slot width to prevent the positioner pin from re-entering a previous stop position after the positioner pin has moved out of the previous stop position.

8. The syringe assembly as defined in claim 3, wherein the valve port positioner is substantially sleeve shaped and is radially positioned substantially within a portion of the piston assembly.

9. The syringe assembly as defined in claim 1, further comprising:

a needle seat retainer adjacent the needle end of the cylinder body for releasably retaining the needle seat in the initial retained position.

10. The syringe assembly as defined in claim 1, further comprising:

a push plate secured to the push plate end of the hollow shaft for applying an axial force to the hollow shaft with an operator finger.

11. The syringe assembly as defined in claim 1, further comprising:

an atmosphere port near the push plate end of the hollow shaft for conducting air between the shaft passageway and the atmosphere external to the syringe assembly.

12. The syringe assembly as defined in claim 1, wherein the connector further comprises:
- a male connector secured to the needle seat; and
- a female connector secured to the hollow shaft for selectively engaging the male connector.

13. A syringe assembly for retracting a needle seat, comprising:
- a cylinder body having a needle end and an opposing end, the cylinder body having a central axis and an internal throughbore extending between the needle end and the opposing end;
- a needle seat in sealed engagement with the cylinder body when the needle seat is in an initial retained position, and the needle seat being selectively moveable from the initial retained position to a needle seat retracted position;
- a needle seat retainer adjacent the needle end of the cylinder body for retaining the needle seat in the initial retained position;
- a piston assembly positioned within the internal through bore of the cylinder body and having a needle end and a shaft end, the piston assembly including a piston for axial movement along the central axis within the internal throughbore, and a shaft receptacle within the shaft end of the piston assembly, and the piston assembly sealing between the piston and an inner wall of the cylinder body while axially moving within the internal throughbore;
- a hollow shaft having a piston end and a push plate end, the piston end positioned within the shaft receptacle and axially moveable relative to the piston assembly, and the push plate end including a push plate secured thereto and an atmosphere port for conducting air between a shaft passageway and the atmosphere external to the syringe assembly, the hollow shaft moveable relative to the cylinder body for axially moving the piston assembly within the through bore of the cylinder body;
- a connector secured to each of the piston end of the hollow shaft and the needle seat for selectively attaching the needle seat to the hollow shaft subsequent to the hollow shaft being moved to the valve closed position;
- a rear seal cap in sealing engagement with the opposing end of the cylinder body and with the hollow shaft for effecting an annular chamber inside of the cylinder body, outside the shaft, and between the piston assembly and the rear seal cap; and
- a valve assembly including (a) one or more valve assembly seals for sealing between the piston and an outer surface of the hollow shaft, (b) a valve port in the hollow shaft for conducting air between the annular chamber and the shaft passageway when the valve assembly is in the at least one valve opened positions, (c) a valve port positioner for regulating axial movement of the hollow shaft relative to the one or more valve assembly seals and thereby regulating axial movement of the valve port relative to the one or more valve assembly seals, the valve assembly operable between the at least one valve opened position for evacuating air from within the annular chamber and the valve closed position for prohibiting the entry of air into the annular chamber such that movement of the piston assembly creates a vacuum in the annular chamber to automatically move the needle seat to the needle seat retracted position.

14. The syringe assembly as defined in claim 13, wherein the valve port positioner further comprises:
- a pin guide slot for regulating movement of a positioner pin within the pin guide slot, the pin guide slot being substantially W-shaped and having five stop positions, each for axially positioning the positioner pin relative to the pin guide slot during successive axial movements of the hollow shaft relative to the piston assembly, and wherein a final axial movement moves the valve assembly from one of the at least one valve opened position to the valve closed position to prevent air from entering the annular chamber as the piston assembly is moved from the opposing end of the cylinder body toward the needle end of the cylinder body; and
- the positioner pin secured to the other of the piston end of the hollow shaft and the piston assembly, the positioner pin moving within the pin guide slot during movement of the valve assembly between the at least one valve opened position and the valve closed position.

15. The syringe assembly as defined in claim 13, wherein the valve port positioner further comprises:
- a pin guide slot for regulating movement of a positioner pin within the pin guide slot, the pin guide slot being substantially V-shaped and having three stop positions, each stop position for axially positioning the positioner pin relative to the pin guide slot during successive axial movements of the hollow shaft relative to the piston assembly, and wherein a final axial movement of the positioner pin within the pin guide slot moves the valve assembly from one of the at least one valve opened position to the valve closed position to prevent air from entering the annular chamber as the piston assembly is moved from the opposing end of the cylinder body toward the needle end of the cylinder body; and
- the positioner pin for moving within the pin guide slot during movement of the valve port between each of the at least one valve opened positions and the valve closed position.

16. The syringe assembly as defined in claim 13, wherein the valve port positioner further comprises:
- a guide pin check-switch to prevent a positioner pin from moving to a previous stop position in a guide pin slot.

17. A method of operating a syringe with a needle seat sealingly engaged with and retractable into a cylinder body having an internal through bore extending between a needle end and an opposing end, the method comprising:
- sealingly engaging the needle seat with the cylinder body, the needle seat being movable from an initial retained position to a needle seat retracted position;
- releasably retaining the needle seat in the initial retained position;
- positioning a piston assembly within the cylinder body, the piston assembly including a piston moveable within the through bore of the cylinder body;
- positioning a piston end of a hollow shaft within a shaft receptacle of the piston assembly, the hollow shaft being axially moveable relative to the piston assembly to operate a valve assembly between a valve opened position for evacuating air from within an annular chamber within the cylinder body surrounding the hollow shaft and a valve closed position for prohibiting the entry of air into the annular chamber, the hollow shaft being moveable relative to the cylinder body for axially moving the piston assembly;
- inserting a needle into a fluid source;

thereafter applying a fluid drawing force to the hollow shaft to move the piston assembly from the needle end of the cylinder body toward the opposing cap end, thereby drawing fluid through the needle seat into a fluid chamber inside of the cylinder body substantially between the needle seat and the piston assembly, and simultaneously displacing air from the annular chamber in the cylinder body through the valve assembly and the hollow shaft;

thereafter removing the needle from the fluid source;

thereafter inserting the needle into a fluid repository;

thereafter applying an axial force to the hollow shaft for sequentially (a) moving the hollow shaft toward the piston assembly to move the valve assembly from the valve opened position to the valve closed position, (b) moving the piston assembly toward the needle end of the cylinder body for discharging fluid from the fluid chamber through the needle and simultaneously expanding the annular chamber in the cylinder body, thereby lowering air pressure in the annular chamber of the cylinder body, (c) connecting a first connector secured to the needle seat to a second connector secured to at least one of the hollow shaft and the piston assembly; and relaxing the axial force to automatically disengage the needle seat from the cylinder body and move the piston assembly and the connected needle seat from the initial retained position to the needle seat retracted position.

18. The method of operating a syringe as defined in claim 17, further comprising:

releasably retaining the needle seat in the initial retained position with a needle seat retainer.

19. The method of operating a syringe as defined in claim 17, further comprising:

positioning an atmosphere port in the hollow shaft external to the cylinder body to evacuate air from within the annular chamber through the hollow shaft and the atmosphere port.

20. The method of operating a syringe as defined in claim 17, further comprising:

sealingly engaging a rear seal cap with the opposing end of the cylinder body and in sealing engagement with the moveable hollow shaft.

21. The method of operating a syringe as defined in claim 17, further comprising:

providing a shaft passageway through the hollow shaft for conducting air between the annular chamber and the atmosphere external to the syringe assembly when the hollow shaft is in the valve opened position;

plugging the piston end of the shaft passageway; and sealing the valve assembly between the piston and an outer surface of the hollow shaft with one or more valve assembly seals.

22. The method of operating a syringe as defined in claim 21, wherein moving the valve assembly from the valve opened position to the valve closed position further comprises:

providing a valve port in the hollow shaft for conducting air between the annular chamber and the shaft passageway when the valve assembly is in the valve opened position; and regulating axial movement of the hollow shaft and thereby movement of the valve port, relative to the one or more valve assembly seals using a valve port positioner.

23. The method of operating a syringe as defined in claim 22, wherein regulating movement of the valve port using a valve port positioner further comprises:

regulating movement of a positioner pin within a pin guide slot provided substantially in one of the piston end of the hollow shaft and the piston assembly; and securing a positioner pin to the other of the piston end of the hollow shaft and the piston assembly; and moving the positioner pin within the pin guide slot during movement of the valve assembly between the valve opened position and the valve closed position.

24. The method of operating a syringe as defined in claim 23, wherein moving the positioner pin within the pin guide slot further comprises:

forming the pin guide slot substantially as a W-shaped slot having five stop positions, each for positioning the positioner pin relative to the pin guide slot during successive axial movements of the hollow shaft relative to the piston assembly; and moving the valve port relative to one or more valve assembly seals to move the valve assembly from the valve opened position to the valve closed position during a final axial movement of the positioner pin within the pin guide slot.

25. The method of operating a syringe as defined in claim 23, wherein moving the positioner pin within the pin guide slot farther comprises:

forming the pin guide slot substantially as a V-shaped slot having three stop positions, each stop position for positioning the positioner pin relative to the pin guide slot during successive axial movements of the hollow shaft relative to the piston assembly; and moving the valve port relative to the one or more valve assembly seals to move the valve assembly from the valve opened position to the valve closed position during a final axial movement of the positioner pin within the pin guide slot to prevent air from entering the annular chamber as the piston assembly is moved from the opposing end of the cylinder body toward the needle end of the cylinder body.

26. The method of operating syringe assembly as defined in claim 23, further comprising:

forming the valve port positioner from a pliable material; and providing at least a portion of a pin guide slot with a variable slot width to prevent the positioner pin from re-entering a previous stop position after the positioner pin has moved out of the previous stop position.

* * * * *